United States Patent [19]

Starnes

[11] Patent Number: 5,595,344

[45] Date of Patent: Jan. 21, 1997

[54] SURGICAL INSTRUMENT CLEANING DEVICE

[76] Inventor: Gary D. Starnes, 2524 Castle, Burleson, Tex. 75028

[21] Appl. No.: 397,394

[22] Filed: Mar. 2, 1995

[51] Int. Cl.⁶ .................................................. B05B 7/04
[52] U.S. Cl. .......................... 239/307; 239/310; 251/295
[58] Field of Search ................................ 239/310, 302, 239/10, 63, 307, 304; 251/295, 57, 129.04

[56] References Cited

U.S. PATENT DOCUMENTS

| 2,542,855 | 2/1951 | Willison | 239/302 X |
|---|---|---|---|
| 2,966,329 | 12/1960 | Burnworth | 251/295 X |
| 3,383,044 | 5/1968 | Norstrud et al. | 239/310 X |
| 3,536,294 | 10/1970 | Rodriguez | 251/295 X |
| 4,238,074 | 12/1980 | Coones | 239/310 X |
| 4,946,107 | 8/1990 | Hunt | 239/585 |
| 5,028,017 | 7/1991 | Simmons | 239/135 X |
| 5,279,448 | 1/1994 | Hanlin et al. | 239/310 X |

FOREIGN PATENT DOCUMENTS

| 2503446 | 11/1975 | Germany | 251/295 |
|---|---|---|---|
| 2651885 | 5/1979 | Germany | 239/310 |

*Primary Examiner*—Kevin Weldon
*Attorney, Agent, or Firm*—Young & Basile, P.C.

[57] ABSTRACT

A device for cleaning surgical instruments uses water from a main water supply wherein the device is capable of delivering a low volume of water at high pressure to the surgical instrument. The device has a pump for boosting a water solution pressure to approximately 85 psi before delivering the water solution to a spray nozzle. A manually operated dual injection system introduces a detergent or an instrument milk solution with the water through a venturi valve on the inlet side of the pump. Air bellows in the form of foot pedals actuate the dual injection system.

9 Claims, 1 Drawing Sheet

SURGICAL INSTRUMENT CLEANING DEVICE

FIELD OF THE INVENTION

The present invention relates to a surgical instrument cleaning device.

BACKGROUND OF THE INVENTION

After each use of a surgical instrument, it is imperative that the surgical instrument is washed and sterilized thoroughly to prevent the transmission of disease-causing contaminants to subsequent patients or medical personnel. The process of sterilizing surgical instruments after surgery consists of several steps. The first step is to "rough clean" the instruments. The purpose of this invention is to assist in this first stage of cleaning.

Many surgical instruments contain cavities or channels that are difficult or impossible to reach with current cleaning devices. Therefore, some surgical instruments can only be cleaned externally. In addition, many current devices for cleaning surgical instruments require a large quantity of water to clean the instruments. It is common for current devices to operate by using a minimum of 2.5 gallons of water a minute when cleaning the surgical equipment. It is the intention of this invention to provide a device that is capable of cleaning internal channels of the surgical instrument. It is also the intention to increase the existing water pressure such that less water can be used than with current devices, while providing effective cleaning ability. It is further an intention of this invention to provide a means for introducing cleaning and lubricating fluids to the device such that the resulting water and fluid solution has an increased pressure when it is sprayed on the surgical instruments.

SUMMARY OF THE INVENTION

The invention uses increased water pressure to flush away foreign particles off of surgical instruments, through the use of a hand held spray wand. The hand held spray wand allows the high pressure water to be directed into hard to reach cavities and channels of such surgical instruments as a Kerrison Rongeurs. Detergent can also be manually selected to help in the cleaning. Instrument milk, a synthetic surgical instrument lubricant, can also be manually selected after cleaning.

A water inlet line connected directly to the hospital's main water supply directs water to a pump assembly at a predetermined pressure. The pump assembly is equipped with a pressure switch that cycles on and off when the water pressure is below or above a particular water pressure. The pump boosts the water pressure to a predetermined maximum pressure. The water is then delivered to a water line attached to a spray wand at the predetermined maximum pressure.

The surgical instrument cleaning device is also equipped with a dual injection system that mixes either detergent or instrument milk into the water at a point prior to entering the pump. Introduction of either the detergent or instrument milk into the water delivery line is activated by a pair of air bellows in the form of foot pedals. When a particular foot pedal is depressed, a solenoid valve allows either the detergent or the instrument milk to flow from their respective bottles into the water entry line.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawing in which.

DESCRIPTION OF THE PREFERRED EMBODIMENT

Figure 2:
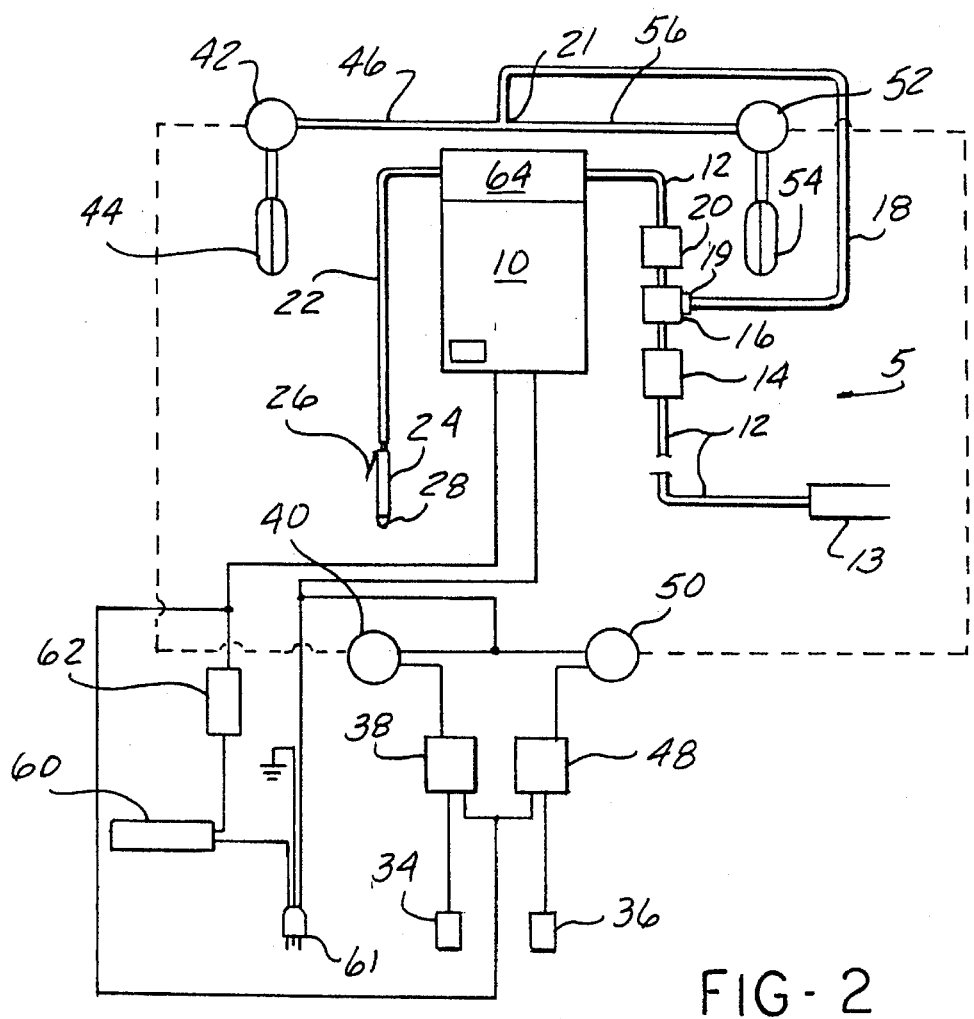
FIG. 2 is a schematic illustration of the present invention in the form of a fluid system, a pump, and the associated circuit diagram with the essential elements of high pressure equipment in accordance with the invention.

First, looking at the schematic illustration of FIG. 2, the surgical instrument cleaning device 5 of the present invention includes a pump 10 communicating to a source of water 13 through conduit 12. The source of water is the main water supply 13 at the hospital or clinic. The water pressure from the main water supply can vary greatly and usually is between 20 and 65 psi. In order to maintain a constant water pressure entering the pump 10, a pressure regulator 14 is disposed in the water conduit 12 before the pump 10. Pressure regulator 14 is set to only allow a constant water pressure of 25 psi water to enter a venturi valve 16. Venturi valve 16 creates a vacuum in a connecting conduit 18 as water flows through the venturi valve 16. The purpose of the vacuum and conduit 18 will be discussed further. As the water exits the venturi valve 16, the water then enters a check valve 20 which allows water to flow in one direction only, that is toward the pump 10. Water enters into the pump 10 from conduit 12 at a pressure of 25 psi. The pump 10 boosts the pressure of the water to 85 psi before exiting the pump 10. The pressurized water exits the pump 10 through conduit 22 at a pressure of 85 psi. Included within pump assembly 10, there is a pressure switch 64 that cycles on, when the water pressure drops below 45 psi, and shuts off the pump 10 when the water pressure reaches 85 psi. The pressure switch 64 provides a safety feature for the device 5 as well as provides a conservation feature for the pump 10.

At a distal end from the pump 10, conduit 22 fluidly communicates with a dispensing means such as a spray wand 24. Conduit 22 delivers the water from pump 10 to the spray wand 24. The spray wand 24 is equipped with an open and close valve 26 that is normally closed and hand operated by a manual lever 26. Water is delivered to the spray tip 28 when the manual valve 26 on spray wand 24 is opened. When valve 26 is initially open the water pressure in conduit 22 and spray wand 24 decreases temporarily before increasing again to 85 psi. Therefore, the water pressure exiting the wand tip 28 may vary from 60 to 85 psi.

Figure 1:
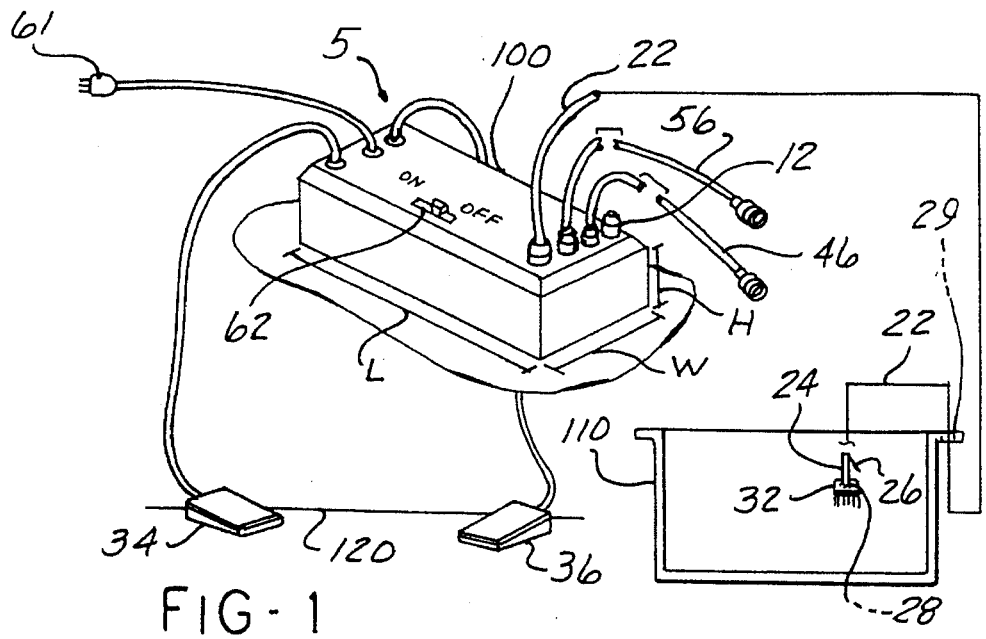
FIG. 1 is a perspective view of a surgical instrument cleaning device according to the preferred embodiment.

The spray tip 28 is designed to spray a fine stream of water where the spray wand 24 and tip 28 can be hand held and manually positioned so that different portions or cavities of the surgical instrument are cleaned. The spray tip 28 may also include attachment means, such as a conventional lure lock, for connecting the spray wand 24 directly onto the surgical instrument. The spray tip 28 also may include a brush 32 that is threadably attached to the tip 28. The brush 32, as shown in FIG. 1, helps in cleaning and also acts as a splash shield when instruments are held close to the tip 28 during the cleaning process.

The surgical instrument cleaning device 5 is also equipped with a dual injection system that mixes either detergent, instrument milk, or other chemical fluid into the water for delivery to the tip 28. The dual injection system includes common conduit 18 having one end 19 in fluid communication with venturi valve 16 and a distal end 21 in communication with a conduit 46 fluidly connected to a container 44 of detergent and also in communication with a conduit 56 fluidly connected to a container 54 having instrument milk. It is within the scope of the invention that containers 44 and 54 may contain any appropriate cleaning and/or lubricating fluid.

Distal end 21 of conduit 18 generally meet conduits 46 and 56 at a T-connection. Disposed in the conduit lines 46 and 56 are normally closed solenoids 42 and 52 respectively. Normally closed solenoids 42 and 52 prevent fluid from one container mixing with a fluid from a second container. Solenoids 42 and 52 are respectfully controlled by foot pedals 34 and 36.

Individual foot pedal 34 controls the release of detergent in container 44 and individual foot pedal 36 controls the release of instrument milk in container 54. The foot pedals 34 and 36 are air bellows that when depressed, supply air pressure that closes the circuits to the respective air switches 38 and 48. The air switches 38 and 48 then energize a respective field coil 40 and 50 that is mounted onto the respective normally closed solenoid valve 42 and 52. When a particular field coil is energized, the respective solenoid valve opens and allows either detergent or instrument milk to flow from their respective bottles, through their respective conduits 46 and 56, and into common conduit 18. The vacuum created by venturi valve 16 causes the fluid from either conduit 46 or 56 to flow into common conduit 18, rather than proceeding to an opposing conduit and to another container of fluid.

Looking at each mixture individually, for example, if detergent is desired to be mixed with the water, foot pedal 34 is depressed which supplies air pressure that closes a circuit on air switch 38. The circuit on the air switch is a normally open circuit, therefore, when the air switch circuit 38 is closed, field coil 40 is energized. The field coil 40 is mounted onto normally closed solenoid valve 42. The solenoid valve 42 opens when field coil 40 is energized, and allows detergent located in container or bottle 44 to flow through conduit 46. Conduit 46 is connected directly to conduit 18 at T-connection 21. As a result of the vacuum created by venturi valve 16 within conduit 18, the detergent flows through conduit 18 to the venturi valve 16 and into the main conduit line 12, thereby mixing with water as it enters the pump 10. Check valve 20 disposed in line 18 ensures that the water and detergent solution in conduit 12 flows toward pump 10 and cannot flow back into conduit 18.

Instrument milk can also be injected into the pump in the same manner as detergent. If instrument milk is desired, foot pedal 36 is depressed which supplies air pressure that closes normally open air switch 48. When air switch circuit 48 is closed, it energizes field coil 50 that is mounted onto normally closed solenoid valve 52. When the solenoid valve opens, instrument milk is allowed to flow from its particular bottle or container 54 and into conduit line 56. Line 56 is directly in communication with conduit 18 at T-connection 21. The vacuum in conduit 18 produced from the venturi valve 16 forces the instrument milk to flow into conduit 18, through venturi valve 16 and into main conduit 12 leading to pump 10. Check valve 20 is disposed in line 12 between venturi valve 16 and the pump, therefore the water and instrument milk solution is subject to flow in only one direction.

The surgical instrument cleaning device 5 is electrically operated from a power source having 110 VAC 61. A circuit breaker 60 is included to protect the energized circuit. A manual on/off switch 62 is provided to energize or deenergize the device 5.

As a result of this system, the surgical instrument cleaning device of the present invention operates on approximately ⅓ gallon of water per minute, whereas most current machines operate at 2.5 gallons of water per minute at a minimum. The low volume of water greatly reduces splash when cleaning the instruments in addition to preserving water.

As shown in FIG. 1, the surgical instrument cleaning device also has the advantage of being a compact unit that can be stored or permanently positioned under a sink 110 used as the cleaning area. The pump 10, pressure switch 64, pressure regulator 14, venturi valve 16, check valve 20 and solenoid valves 42 and 52 are housed in a small unit approximately 7 inches wide (W), 12 inches long (L) and 5 inches high (H). The various conduit lines from the water source and the detergent and instrument milk extend from the unit 100. Conduit 22 that leads to the spray wand 24 can pass through an aperture 29 through the sink 110 so that the wand 24 and brush 32 have access to a surgical instrument located in the sink 110. The foot pedals 34 and 36 also extend from unit 100 so that pedals 34, 36 may be placed on the ground or floor 120 so that the pedals are accessible to a user's feet.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A surgical instrument cleaning device comprising:

a pump having an inlet conduit fluidly connecting said pump to a water source, and an outlet conduit fluidly connecting said pump to a dispensing means;

a dual injection means for mixing another fluid with the water in the inlet conduit before the water enters the pump; and an actuating means for selectively permitting the other fluid to flow into the inlet conduit for mixing with the water, wherein the actuating means includes a foot actuating bellows with a normally open air switch, wherein the air bellows supplies air pressure to close the air switch to permit the other fluid to flow into the inlet conduit.

2. The surgical instrument cleaning device of claim 1 wherein the device further comprises a pressure regulator disposed in the inlet conduit for maintaining inlet water pressure less than a predetermined pressure.

3. The surgical instrument cleaning device of claim 2 wherein the device further comprises a venturi valve disposed in the inlet conduit downstream of the pressure regulator.

4. The surgical instrument cleaning device of claim 3 wherein the dual injection means fluidly communicates with the inlet conduit at the venturi valve.

5. The surgical instrument cleaning device of claim 4 wherein the device further comprises a pressure switch to maintain fluid pressure in the pump between approximately 45 to 95 psi.

6. The surgical instrument cleaning device of claim 5 wherein the pressure regulator maintains the inlet water pressure at a maximum of 25 psi.

7. The surgical instrument cleaning device of claim 6 wherein the device is housed in a compact unit capable of positioning under a sink.

8. The surgical instrument cleaning device of claim 4 wherein a normally closed solenoid is disposed between the other fluid and the common conduit.

9. A surgical instrument cleaning device surgical instrument cleaning device comprising:

- a pump having an inlet conduit fixedly connecting said pump to a water service, and an outlet conduit fixedly connecting said pump to a dispensing means;
- a duel injection means for mixing one of at least two fluids stored in containers with the water in the inlet conduit before the water enters the pump;
- a pressure regulator disposed in the inlet conduit for maintaining inlet water pressure less than a predetermined pressure;
- a venturi valve disposed in the inlet conduit downstream of the pressure regulator, wherein the dual injection means fluidly communicates with the inlet conduit at the venturi valve and the dual injection means includes a common conduit fluidly connected to the at least two containers of the fluid at a first end and the venturi valve at a distal end; and
- an actuating means for selectively opening one of the containers so that fluid can flow through the common conduit, venturi valve and into the inlet conduit, wherein a normally closed solenoid is disposed between the containers of fluid and the common conduit and wherein the actuating means includes a foot actuating air bellows, a normally open air switch, and a field coil, wherein the air bellows supplies air pressure that closes the air switch, which energizes the field coil to open the normally closed solenoid valve, whereby fluid from one of the containers can flow to the common conduit, venturi valve and into the inlet conduit.

* * * * *